(12) United States Patent
Heath et al.

(10) Patent No.: US 8,644,978 B1
(45) Date of Patent: Feb. 4, 2014

(54) MACHINING APPARATUS AND METHOD OF MAKING ENDODONTIC INSTRUMENTS

(75) Inventors: Derek E. Heath, Vero Beach, FL (US); Brian J. Little, Jonesborough, TN (US); Steve A. Treadway, Jonesborough, TN (US)

(73) Assignee: D & S Dental, LLC, Johnson City, TN (US)

( * ) Notice: Subject to any disclaimer, the term of this patent is extended or adjusted under 35 U.S.C. 154(b) by 293 days.

(21) Appl. No.: 13/010,450

(22) Filed: Jan. 20, 2011

Related U.S. Application Data

(60) Provisional application No. 61/296,697, filed on Jan. 20, 2010.

(51) Int. Cl.
  *G06F 19/00* (2011.01)
  *B24B 1/00* (2006.01)
  *B24B 7/19* (2006.01)
  *B24B 7/30* (2006.01)
  *A61C 5/02* (2006.01)

(52) U.S. Cl.
  USPC .............................. 700/164; 451/48; 433/102

(58) Field of Classification Search
  USPC .............................. 700/164; 451/48; 433/102
  See application file for complete search history.

(56) References Cited

U.S. PATENT DOCUMENTS

| | | | |
|---|---|---|---|
| 4,745,557 A | 5/1988 | Pekar et al. | |
| 5,464,362 A * | 11/1995 | Heath et al. | 451/48 |
| 5,527,205 A | 6/1996 | Heath et al. | |
| 5,628,674 A | 5/1997 | Heath et al. | |
| 5,655,950 A | 8/1997 | Heath et al. | |
| 5,762,541 A * | 6/1998 | Heath et al. | 451/48 |
| 5,941,760 A * | 8/1999 | Heath et al. | 451/48 |
| 5,984,679 A * | 11/1999 | Farzin-Nia et al. | 433/102 |
| 6,149,501 A | 11/2000 | Farzin-Nia et al. | |
| 6,428,317 B1 * | 8/2002 | Abel | 433/102 |
| 6,445,971 B1 * | 9/2002 | Gottschalk et al. | 700/159 |
| 6,732,558 B2 * | 5/2004 | Butscher et al. | 72/21.4 |
| 7,018,205 B2 * | 3/2006 | Abel | 433/102 |
| 7,202,439 B2 * | 4/2007 | Ishiwata et al. | 219/69.14 |
| 7,731,498 B2 * | 6/2010 | McSpadden | 433/102 |
| 7,738,977 B2 * | 6/2010 | Weinhofer et al. | 700/61 |
| 8,103,376 B2 * | 1/2012 | Wang et al. | 700/195 |
| 2003/0199236 A1 * | 10/2003 | Aloise et al. | 451/48 |
| 2005/0113962 A1 | 5/2005 | Matthews et al. | |
| 2006/0228668 A1 * | 10/2006 | McSpadden | 433/102 |
| 2006/0265858 A1 * | 11/2006 | McSpadden | 29/558 |
| 2007/0003902 A1 * | 1/2007 | Castellini | 433/98 |
| 2009/0197217 A1 * | 8/2009 | Butscher et al. | 433/20 |

OTHER PUBLICATIONS

ZP200 Vertical Lift 'wedge' Table 192-590014 N3/UK.*
Yokogawa Electric Corp., Dynaserv Instruction Manual, IM 71M01D03-01E, 10th Edition Oct. 23, 2006. Publisher: Yokogawa Electric Corp., 2-9-32, Nakacho, Musashino-shi, Tokyo, Japan 180-8750.
Dynomax, Inc., Dynomax Spindle Manual, Mundelein, IL 60060.
Parker Hannifin Corp., Electromechanical Positioning Systems, Manual No. 100-5324-01 Rev. 4, ZP200 Series Product Manual, Feb. 23, 2007, Irwin, PA 15642.
Parker Hannifin Corp., Electromechanical Positioning Systems, Manual No. 100-5320-01 Rev. 5, 404/406XR Series Product Manual, Jan. 12, 2006, Irwin, PA 15642.

* cited by examiner

*Primary Examiner* — Mohammad Ali
*Assistant Examiner* — Ziaul Karim
(74) *Attorney, Agent, or Firm* — Luedeka Neely Group, P.C.

(57) ABSTRACT

A machining apparatus and method for fabricating endodontic instruments adapted for use in performing root canal procedures is disclosed. The machining apparatus includes computer numerical control (CNC) machining that automates much of the fabrication process. The disclosed machining apparatus and method is programmable to efficiently produce varying configurations of endodontic instruments on the same machining apparatus.

9 Claims, 15 Drawing Sheets

MACHINING APPARATUS AND METHOD OF MAKING ENDODONTIC INSTRUMENTS

CROSS-REFERENCE TO RELATED APPLICATIONS

This application claims priority to provisional application No. 61/296,697 filed Jan. 20, 2010 entitled Machining Apparatus and Method of Making Endodontic Instruments, the entire contents being incorporated herein by reference.

FIELD

The present invention relates to the field of endodontic instruments. More particularly, this invention relates to a machining apparatus and method for fabricating endodontic instruments adapted for use in performing root canal procedures on teeth.

BACKGROUND

In root canal procedures, the crown of a diseased tooth is opened so as to permit the canal to be cleaned and filled. A series of root canal instruments, each of increasing or decreasing diameter, are then used to enlarge, clean out, and smooth the walls of the root canal. These root canal instruments, also known as files, must be composed of a high strength, resilient metal capable of sufficient flexing for following the normal curvatures of the root canal. Each instrument has an elongate shank having a lower working length. Historically, dentists have used elongate, tapered endodontic files with the working length having helical cutting edges to remove the soft and hard material from within and adjacent the root canal area. However, the working length of the endodontic files can have a wide range of configurations such as helical or non-helical flutes, tapered or un-tapered working lengths, different shaped cross sections, and working lengths having varying pitch levels for the flutes.

Endodontic instruments as described above were conventionally fabricated by permanently twisting a stainless steel rod, and the angles formed between the surfaces would form the cutting edges which would spiral along the working length of the instrument. Machining processes were then developed wherein a cylindrical rod of stainless steel was moved past a rotating grinding wheel while the rod was slowly rotated.

As shown in FIG. 1A, in conventional machining apparatuses 1 utilizing the grinding method, the rod 12 is positioned to extend through a feed block 2 and an indexing block 3. The feed block 2 and indexing block 3 are then advanced manually or by using a system of cams and a series of gears so that the rod 12 axially moves past the rotating grinding wheel 4 in the X-coordinate direction. After the rod 12 is advanced past the rotating grinding wheel 4 a distance sufficient to form the first surface of the instrument, a table 5 supporting the components of the machining apparatus 1, including the feed block 2 and indexing block 3, is moved back to its original position along a path as depicted in the arrows below the apparatus 1. The rod 12 is thereafter indexed and again moved past the grinding wheel 4 to form the second surface of the instrument. The process of moving the supporting table 5 and indexing the rod 12 is repeated to form each subsequent surface of the instrument.

One problem associated with the conventional machining apparatuses used in the grinding method is the fact that the grinding wheel has to be movable to fabricate instruments of different configurations. For example, to fabricate instruments having a generally flat working surface, the grinding wheel has to be oriented to rotate about an axis generally parallel to the axis of the advancing rod. However, to fabricate an instrument having helical flutes of an arcuate configuration, the axis of the grinding wheel may be oriented so that the wheel lies in a plane which follows the desired helical configuration of the flutes. Furthermore, the grinding wheel has to be movable vertically to adjust the machining apparatus for fabrication of instruments having different diameters. The fact that the rotating grinding wheel is movable can cause a large amount of vibration of the rotating wheel, resulting in imprecise and faulty instruments. As a result, grinding wheels are often only operated at slower surface speeds in order to reduce vibration. Accordingly, there is a need for a machining apparatus having a fixed grinding wheel rotatable at a higher surface speed to fabricate endodontic instruments.

Another disadvantage of the conventional machining apparatuses used for the grinding method is that the instruments are fabricated in a time consuming, expensive, and imprecise manner. In some operations, after the rotating rod advances past the rotating grinding wheel to form the first surface, an operator has to manually change positioning of components of the machining apparatus and manually index the rod before advancing the rod past the rotating wheel to form the second surface. Manual operation of these steps leads to greater opportunities for human error, especially when indexing the small diameter rods to precise angle measurements. Additionally, conventional machining apparatuses cannot effectively advance the same working surface past the grinding wheel twice to fix cutting errors that occur during a single pass. This is due to the imprecision of the conventional machining apparatuses and their inability to start the rotating rod at the same angular position as was used during the working surface's first pass of the grinding wheel. Accordingly, there is a need for a machining apparatus and method which provides for improved automation and precise fabrication of endodontic instruments.

Yet another disadvantage is that these conventional machining apparatuses are limited in that each machine is often practically limited to manufacturing a single instrument configuration. It was found to be very time consuming and difficult to precisely adjust the positioning of components, change operating parameters, and recalibrate the machine, the adjustments typically being done manually, to switch from producing an instrument of one configuration to an instrument of a second configuration. For example, for instruments having a nontapered working length, the axis of the index block may be horizontal with respect to the axis of the grinding wheel. However, if the instrument has a tapered working length, the axis of the index block may be slightly inclined with respect to the rotational axis of the wheel. Thus, it was found that using multiple conventional machining apparatuses, one for each type of desired configuration, was more advantageous than having to adjust the settings. As files of different diameters, shank lengths, angles of tapering, dimensions of flutes, variety of cross sections, etc. are used in root canal procedures, many different machines were needed to fabricate the various endodontic instruments. Accordingly, there is a need for one machining apparatus that can be utilized to fabricate a variety of instruments that have various dimensions and surface features.

SUMMARY OF THE INVENTION

The present invention provides a machining apparatus for fabricating endodontic instruments having a plurality of instrument configurations. The machining apparatus includes a computer interface, a grinding wheel, and a positioning mechanism. The computer interface is for storing operating parameters of a plurality of cutting configurations, each cutting configuration corresponding to at least one of the plurality of instrument configurations, for selecting one of the plurality of cutting configurations, and for generating control signals based upon the stored operating parameters of the cutting configuration selected. The grinding wheel grinds the endodontic instruments. The positioning mechanism is operable for loading one of the endodontic instruments, for receiving the control signals, and for controlling a translational motion and a rotational velocity of the loaded endodontic instrument as the loaded endodontic instrument is moved past the grinding wheel at least in part in response to the control signals.

According to certain embodiments of the invention, the grinding wheel is disposed on a fixed spindle so that the grinding wheel is in a fixed position operable for fabricating each of the plurality of instrument configurations.

In certain embodiments, the positioning mechanism further includes a linear driving mechanism for providing the translational motion of the positioning mechanism along a horizontal axis, a lift mechanism for providing the translational motion of the positioning mechanism along a vertical axis, and a feed block having a spindle for supporting the loaded endodontic instrument and for providing the rotational velocity of the loaded endodontic instrument. The linear driving mechanism may include a positioning plate disposed on a top surface of the linear driving mechanism for supporting the lift mechanism. The positioning mechanism may also include a pneumatic actuator having a mounting surface disposed on a top surface of the pneumatic actuator for mounting the feed block, the pneumatic actuator for providing positioning of the feed block in one of an engaged position adjacent the grinding wheel and a disengaged position remote from the grinding wheel.

According to certain embodiments, the machining apparatus further includes a dressing mechanism disposed adjacent the grinding wheel for redressing the grinding wheel, and the computer interface is operable for storing measurement calculations of a diameter of the grinding wheel during redressing and for recalibrating the operating parameters of the plurality of cutting configurations based on the measurement calculations.

In other aspects of the invention, the computer interface may include a jog dashboard for manually editing the stored operating parameters of the plurality of cutting configurations. The computer interface may be operable for storing operating parameters of a plurality of tapering configurations, for selecting one of the plurality of tapering configurations, and for generating control signals based upon the stored operating parameters of the tapering configuration selected. The positioning mechanism may include means for automatically loading the endodontic instrument into the positioning mechanism.

According to another embodiment of the invention, a method for fabricating endodontic instruments having a plurality of instrument configurations is disclosed. The method includes the steps of inputting operating parameters representing a plurality of cutting configurations into a computer interface, each of the plurality of cutting configurations corresponding to at least one of the plurality of instrument configurations; loading a first endodontic instrument into a feed block; selecting one of the plurality of cutting configurations from the computer interface; generating control signals based on the cutting configuration selected; receiving the control signals at a positioning mechanism attached to the feed block; and controlling a translational motion and a rotational velocity of the loaded endodontic instrument at least in part in response to the control signals as the loaded endodontic instrument is moved past a grinding wheel for machining flutes onto the loaded endodontic instrument and for producing a first fabricated endodontic instrument having a first instrument configuration.

According to certain embodiments, the method further includes unloading the first fabricated endodontic instrument from the feed block; loading a second endodontic instrument into the feed block; selecting a second one of the plurality of cutting configurations from the computer interface, the second one of the plurality of cutting configurations corresponding to a second instrument configuration different than the first instrument configuration; generating second control signals based on the second cutting configuration selected; receiving the second control signals at the positioning mechanism attached to the feed block; and controlling a translational motion and a rotational velocity of the second loaded endodontic instrument at least in part in response to the second control signals as the loaded endodontic instrument is moved past the grinding wheel for machining flutes onto the second loaded endodontic instrument and for producing a second fabricated endodontic instrument having the second instrument configuration. In certain embodiments, the method includes inspecting the first fabricated endodontic instrument by passing the first fabricated endodontic instrument through an inspection system, and the loading of the second endodontic instrument is dependent on whether the first fabricated endodontic instrument is satisfactory.

According to certain embodiments of the invention, the method includes controlling the translational motion and the rotational velocity of the loaded endodontic instrument as the loaded endodontic instrument is moved past the grinding wheel for tapering the loaded endodontic instrument prior to machining the flutes onto the loaded endodontic instrument.

The controlling of the translational motion and the rotational velocity step may include moving the loaded endodontic instrument in a first pass of the grinding wheel for machining a first working surface according to the operating parameters of the selected cutting configuration; indexing the loaded endodontic instrument after completing the first pass by rotating the loaded endodontic instrument according to the operating parameters of the selected cutting configuration; and moving the loaded endodontic instrument in a second pass of the grinding wheel for machining a second working surface according to the operating parameters of the selected cutting configuration. The controlling the translational motion and the rotational velocity step may also include moving the loaded endodontic instrument in a precision pass of the grinding wheel for removing any cutting errors in the first working surface prior to indexing the loaded endodontic instrument.

In another aspect of the invention, the method includes securing the grinding wheel to a fixed spindle so that the grinding wheel is in a fixed position operable for fabricating each of the plurality of instrument configurations.

According to another embodiment of the invention, a machining apparatus for fabricating endodontic instruments having a plurality of instrument configurations is disclosed. The machining apparatus includes a computer interface, a grinding wheel, and a positioning mechanism. The computer interface is operable for storing operating parameters of a plurality of cutting configurations, each cutting configuration corresponding to at least one of the plurality of instrument configurations, for selecting one of the plurality of cutting configurations, and for generating control signals based upon the stored operating parameters of the cutting configuration selected. The grinding wheel is disposed on a fixed spindle so that the grinding wheel is in a fixed position operable for fabricating each of the plurality of instrument configurations. The positioning mechanism is operable for receiving the control signals and for controlling a translational motion and a rotational velocity of the positioning mechanism. The positioning mechanism includes a linear driving mechanism for providing the translational motion of the positioning mechanism along a horizontal axis based at least in part on the control signals, a lift mechanism for providing the translational motion of the positioning mechanism along a vertical axis at least in part on the control signals, and a feed block having a spindle for loading an endodontic instrument to be fabricated and for providing a rotational velocity of the loaded endodontic instrument based at least in part on the control signals, the feed block for moving the loaded endodontic instrument past the grinding wheel based at least in part on the cutting configuration selected.

In certain embodiments, the stored operating parameters of the plurality of cutting configurations includes tapering parameters, the positioning mechanism for moving the loaded endodontic instrument past the grinding wheel for tapering the loaded endodontic instrument according to the tapering parameters prior to moving the loaded endodontic instrument past the grinding wheel for fluting the loaded endodontic instrument.

BRIEF DESCRIPTION OF THE DRAWINGS

Further advantages of the invention are apparent by reference to the detailed description in conjunction with the figures, wherein elements are not to scale so as to more clearly show the details, wherein like reference numbers indicate like elements throughout the several views, and wherein.

DETAILED DESCRIPTION

Figure 1A:
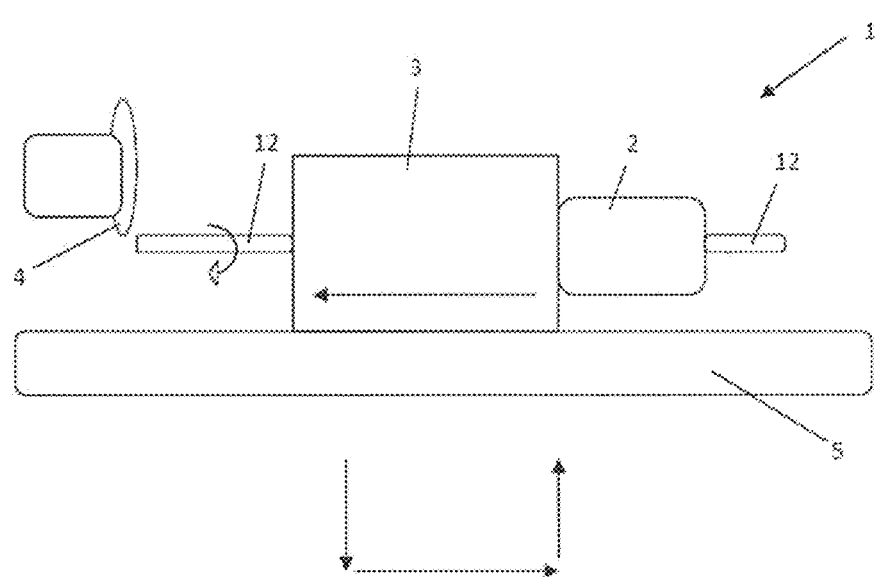
FIG. 1A depicts a conventional machining apparatus as used in the prior art for machining root canal instruments.
Figure 1B:
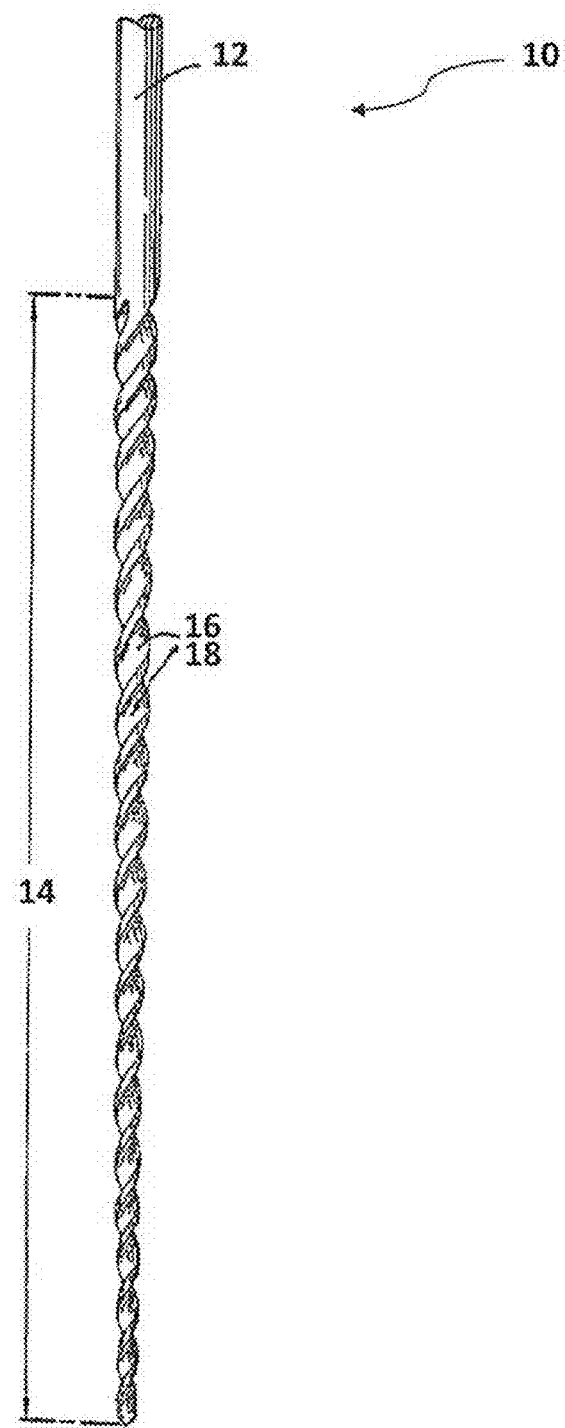
FIG. 1B depicts an endodontic instrument.

Referring to FIG. 1B, an endodontic instrument 10 is illustrated which comprises an elongate shank, preferably in the form of a cylindrical rod 12 composed of stainless steel, nickel-titanium alloy, or other suitable metals or alloys. The rod 12 further includes a working length 14 that may be tapered as illustrated or also un-tapered. The working length 14 of the rod 12 preferably extends from about 2 mm (0.08 inches) to about 32 mm (1.26 inches), but may be longer as needed. The outer peripheral surface of the working length 14 includes continuous helical flutes 16, 18. In alternate embodiments, the working length 14 may include one or more helical flutes, non-continuous flutes, non-helical radial cutting surfaces, and/or other cutting surfaces known to those in the art.

Figure 2:
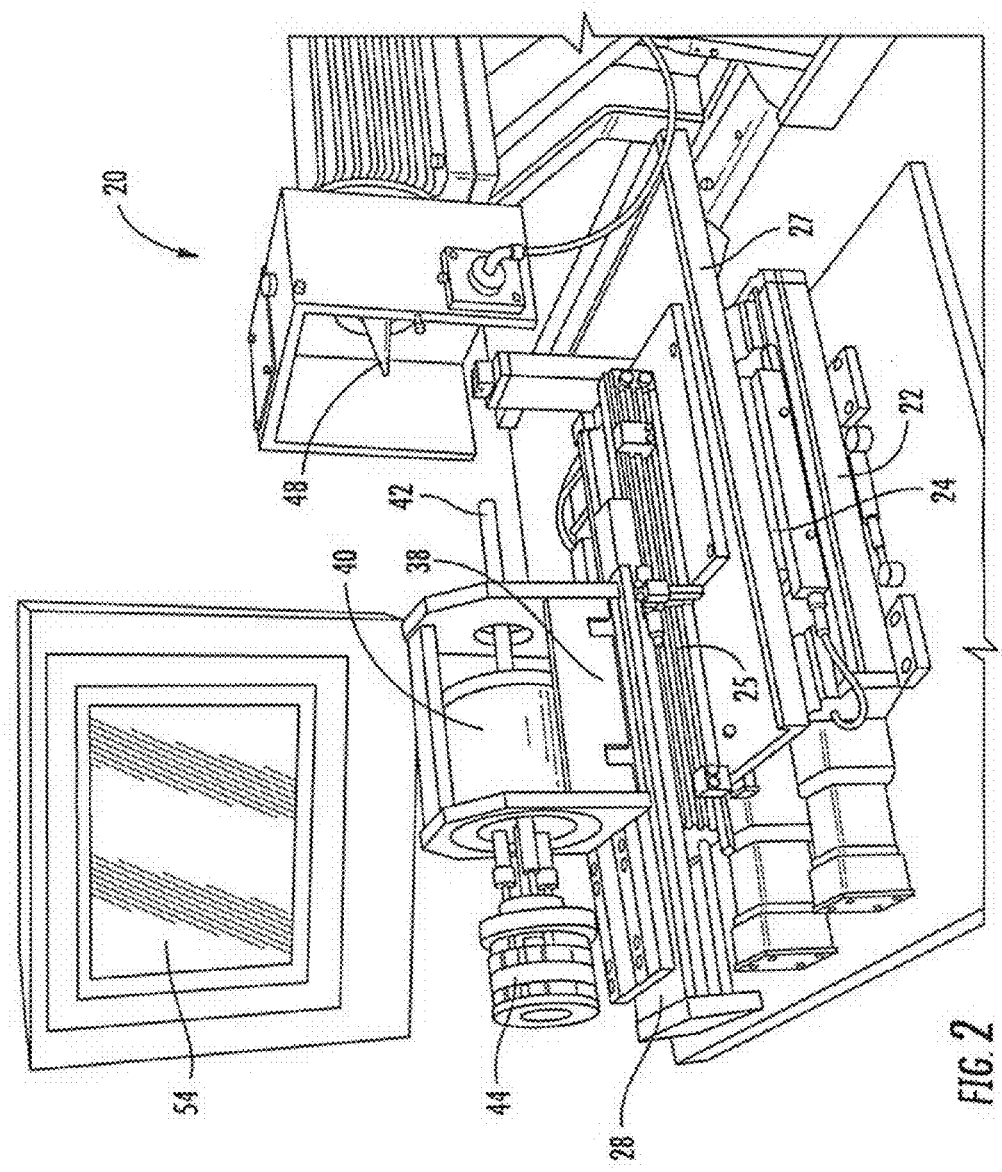
FIG. 2 depicts a machining apparatus according to embodiments of the present invention.
Figure 3:
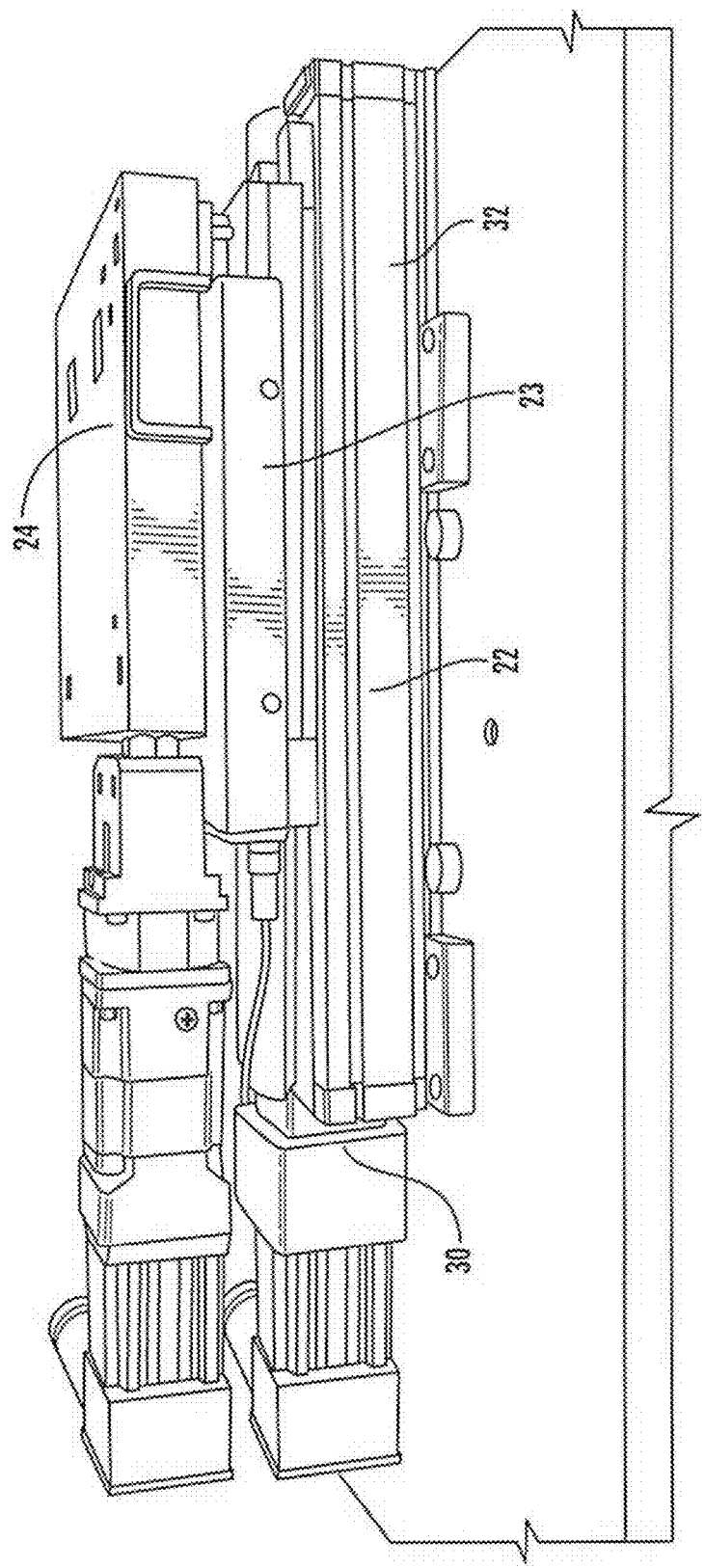
FIG. 3 depicts a linear driving mechanism and lift mechanism according to embodiments of the present invention.
Figure 4:
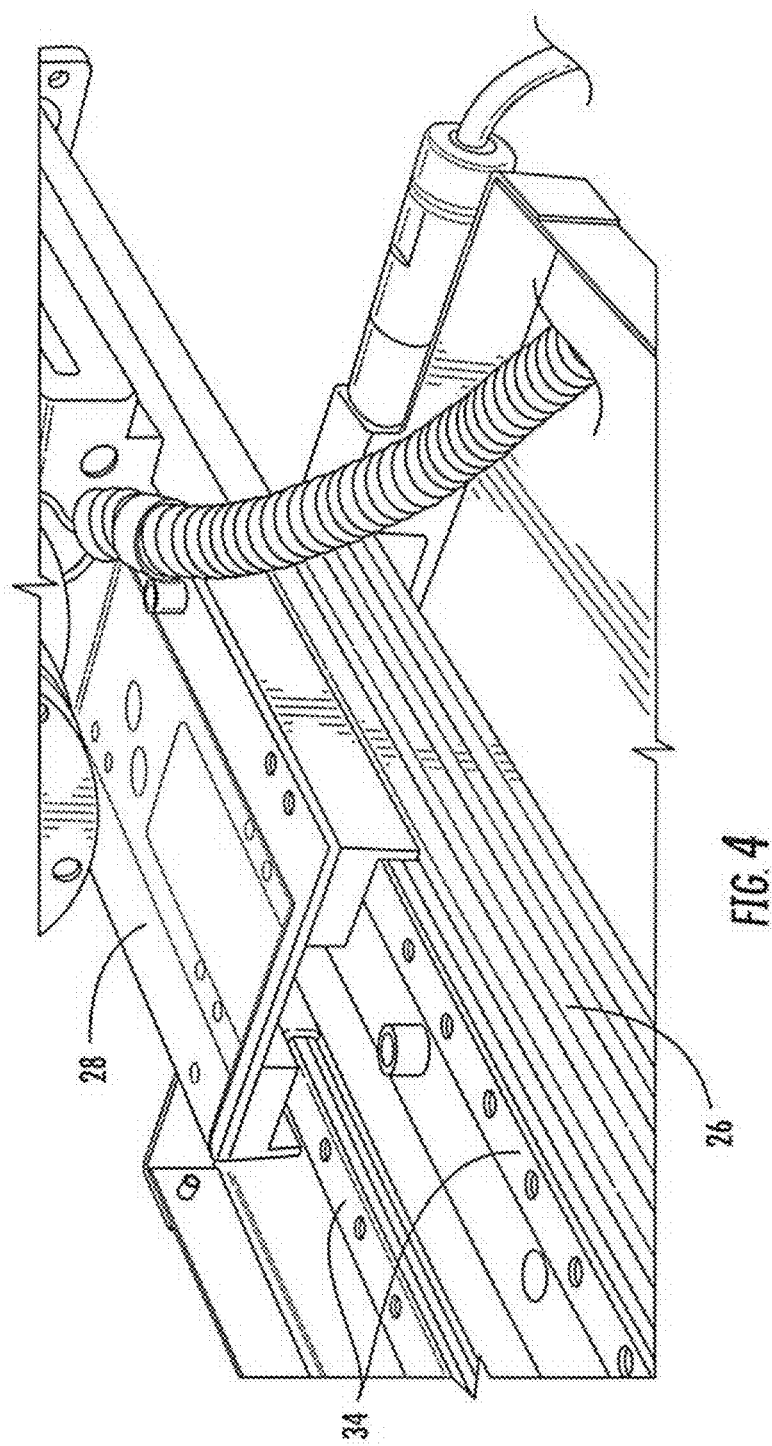
FIG. 4 depicts a pneumatic actuator according to embodiments of the present invention.

FIGS. 2-4 illustrate an embodiment of a machining apparatus 20 movable in X, Y, and Z coordinate directions for fabricating endodontic instruments 10 within which features of the present invention are embodied. However, it should be understood that various configurations of XYZ linear motion systems, also referred to herein as positioning mechanisms, are possible and within the scope of the present invention. In a preferred embodiment, the machining apparatus 20 includes a computer numerical control (CNC) machining system that controls the operating parameters of the machining apparatus 20, automates much of the fabrication process, and allows for precise motion combinations. Thus, the machining apparatus 20 may be quickly programmable for many different precise and efficient endodontic instrument designs.

Referring to FIGS. 2-3, the machining apparatus 20 includes a linear driving mechanism 22 as the system base axis. The linear driving mechanism 22 can be any linear positioning mechanism that provides for precise horizontal movement and positioning of the machining apparatus 20 along the X-axis and a stable mounting surface for supporting additional components of the machining apparatus 20 that are mounted to the linear driving mechanism 22. A non-exclusive example of the driving mechanism 22 is Parker Hannifin's 406XR linear stage positioning slide. As shown in FIG. 3, this particular linear positioning device has a positioning plate 23 used as the mounting surface disposed on the top surface of the linear positioning mechanism 22. This plate 23 is driven by a servo attached to a precision ground ball-screw that precisely drives the plate forward and backward while riding on square rail carriage support bearings that provide high load carrying capabilities. Accordingly, the linear driving mechanism 22 enables precise control of the positioning of the X-axis of the machining apparatus 20 from a proximal end 30 to a distal end 32 as well as providing a stable mounting surface for the components that are mounted on the positioning plate 23.

The machining apparatus 20 also includes a lift mechanism 24 which provides precise vertical movement and positioning of the machining apparatus 20 along the Y-axis. As shown in FIG. 3, the lift mechanism 24 is preferably mounted on the positioning plate 23 of the linear driving mechanism 22. One non-exclusive example of the lift mechanism 24 is Parker Hannifin's ZP 200 "Wedge" Vertical Lift Table. This particular table utilizes a wedge design within the table to convert horizontal motion of the wedges into vertical elevation of the table's platform with no displacement in the horizontal plane. The wedges are driven by a lead-screw that is turned by a servo motor. Re-circulating square rail bearings are incorporated into the "wedge" mechanics to enable reliable dynamic performance without the potential loss of travel encountered with cross roller bearings.

Figure 5:
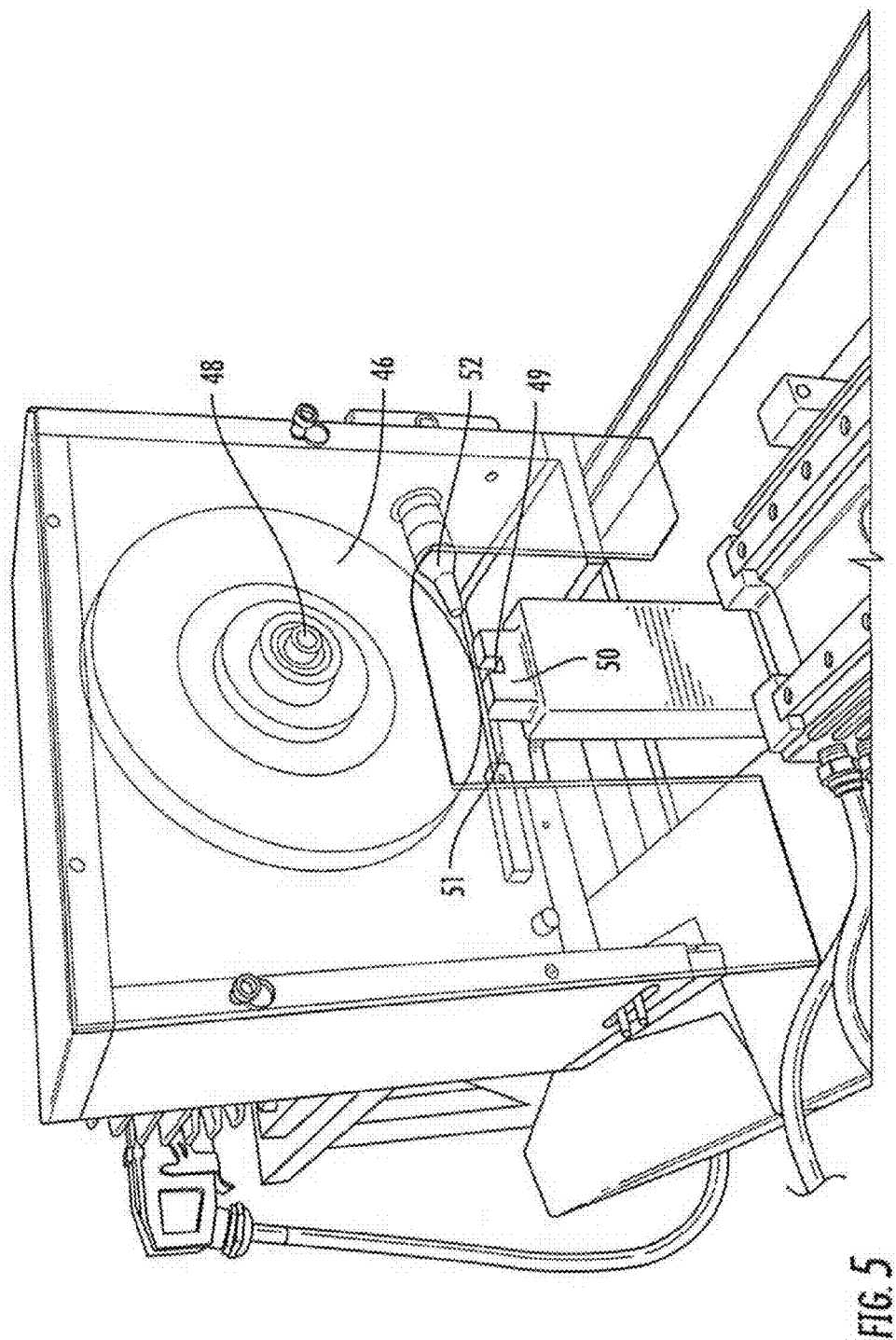
FIG. 5 depicts a grinding wheel according to embodiments of the present invention.

Referring to FIGS. 2, 4, and 5, a pneumatic actuator 26 is mounted on top of the lift mechanism 24 for positioning the rod 12 to be fabricated by the machining apparatus 20 in either an engaged position or a disengaged position. In the engaged position, the pneumatic actuator 24 moves the machining apparatus 20 to adjacent a grinding wheel 46 in order for the rod 12 to be fabricated, for example immediately prior to the start of the instrument fabrication process. In the disengaged position, the pneumatic actuator 24 moves the rod away from the grinding wheel 46, for example immediately following the end of the fabrication process. As shown in FIG. 2, a protective plate 27 may be disposed between the pneumatic actuator and the lift mechanism 24 for providing protection and cover to the linear driving mechanism 22 and lift mechanism 24 components of the machining apparatus 20. A non-exclusive example of the pneumatic actuator 26 is the Parker Hannifin P5SP pneumatic slide. As shown in FIG. 4, re-circulating square rail bearings 34 may be incorporated into the design and are attached to precision ground rails to ensure accurate travel and lateral placement throughout the slide's movement.

Attached to the top surface of the pneumatic actuator 26 is a mounting surface 28, and an axial feed block 38 for positioning the rod 12 from which the endodontic instrument 10 is to be fabricated is secured to the mounting surface 28. Disposed within the axial feed block 38 is a servo motor 40 used to rotate a rod spindle 42 about the z-axis (movement of a rod in the "z-axis" referred to herein is meant to indicate the rotational movement about the rotational axis of the spindle). The spindle 42 includes a drawbar (not shown) disposed within the spindle 42 and a collet (not shown) fastened to the drawbar for holding the rod 12 in place as the spindle 42 rotates. A mounting bracket 44 disposed adjacent the feed block 38 may be used to pull drawbar for locking the collet in place. In certain embodiments, the collet may be replaceable for use with rods 12 of differing diameters. The correct size collet can be fastened through the front of the spindle 42 by threading the collet into the drawbar. In preferred embodiments, the collet includes a nose piece through which the rod 12 to be fabricated extends. Three triangular grippers, or other suitable mechanisms, are utilized to properly position the rod 12 within the spindle 42. The triangular grippers are operable to tightly hold rods of different diameters and center the rod 12 within the nose piece.

In certain embodiments, the rod 12 may be manually inserted into the collet of the spindle 42. In one embodiment, a loading block is used during manual loading that also presets the amount of material exposed on the rod 12 for the grinding operation. Alternatively, rods may be automatically fed into the machine 20 via a bowl feeder, or mechanisms may be added adjacent to the machining apparatus 20 for picking up a rod 12 from a group of rods and transferring the rod 12 using pneumatic slides or robotic arms into the spindle 42. Following insertion of the rod 12 into the spindle 42 of the axial feed block 38, the axial feed block 38 operates to rotate the rod 12 about its axis at a controlled speed.

In a preferred embodiment, the axial feed block 38 is secured to the mounting surface 28 so that the rod 12 is oriented to rotate about an axis substantially parallel to the axis of rotation of a grinding wheel 46 disposed adjacent the distal end 32 of the linear driving mechanism 22. However, in certain embodiments, components of the machining apparatus 20 may be slightly rotated about a vertical and/or horizontal axis so that rod 12 rotates along a slightly different axis than the axis of the grinding wheel 46.

The grinding wheel 46, as shown in FIG. 5, is disposed adjacent the distal end 32 of the linear driving mechanism 22. To allow precise movement of the rod 12 towards the grinding wheel 46, the driving mechanism 22 and lift mechanism 24 are operable as an XY linear motion system. After a rod 12 has been inserted in the spindle 42 and with the pneumatic actuator 26 in the engaged position, the axial feed block 38 may be advanced toward the grinding wheel 46 at a feed rate in the X-axis ranging from about 2 to about 20 inches per minute, preferably about ten inches per minute, while also moving the rod in the Y and/or Z axes, such that the grinding wheel cuts desired cutting surfaces into the rod, such as helical cutting surfaces. The feed rates may be altered depending on the desired configuration of the finished instrument, and the feed rates can be controlled so that it does not have to be the same for each instrument 10 fabricated. The axial feed block 38 and rod 12 may also be programmed to constantly or variably accelerate or decelerate during manufacture of an instrument 10 in order to increase or decrease the pitch of the helical configuration along the length of the instrument 10, to account for varying tapering of the rod 12, or to vary other instrument configuration options by controlling the rate of the interpolated movement of the rod in the X, Y, and/or Z axes as it passes by the grinding wheel 46.

In an alternate embodiment, the machining apparatus 20 may include multiple grinding wheels 46, which may be selectively indexed to adjacent the distal end 32 of the linear driving mechanism 22. The outer periphery of each grinding wheel 46 may have different cutting surfaces to allow different forms to be applied to different instruments 10. For example, one of the indexed grinding wheels 46 may have a flat cross section as opposed to being arcuate so as to form a flat configuration of the flutes.

With reference to FIG. 5, in a preferred embodiment, the grinding wheel 46 is in a fixed position on a fixed wheel spindle 48. A coolant nozzle 52 may also be included adjacent the grinding wheel 46 to provide coolant to the rod 12 while the rod is being moved past the rotating grinding wheel 46. In one embodiment, the grinding wheel 46 is operable to rotate at a surface speed ranging from about 2,000 to about 10,000 feet per minute, preferably rotating at about 6,000 feet per minute. Further, the grinding wheel 46 may be comprised of any material known in the art of grinding, such as aluminum oxide or silicon carbide. The grinding wheel may also have a range of grit size known in the art, but is preferably a relatively fine grit, such as about 220. Because the present invention uses a rigid or fixed grinding wheel 46, the machining apparatus 20 allows for a single set up of the wheel 46 for all configurations of instruments 10 to be produced. In contrast to the wheel orientation changing to alter the configuration of the instruments 10, the programming of the X, Y, and Z coordinate positioning of the rod 12 and axial feed block 38 changes the orientation of the rod 12 moving past the grinding wheel 46 to determine the desired configuration of the cutting surfaces along the working length 14 of the instrument 10.

Preferably, a holding structure 50 is mounted adjacent the engaged position of the pneumatic actuator 26 and positioned proximate the grinding wheel 46 to maintain the positioning of the rod 12 while the rod 12 moves past the grinding wheel 46. The holding structure 50 includes a rod holder 49 configured to receive the rod 12 when the pneumatic actuator 26 is moved into the engaged position and a supporting mechanism 51 disposed above the rod holder 49 for maintaining the proper position of the rod 12 in the rod holder 49. The rod holder 12 preferably includes a V-shaped notch (not shown) for supporting a portion of the rod 12 as the rod moves past the grinding wheel 46. The pneumatic actuator 26 removes the rod 12 from the rod holder 49 when in the disengaged position after the rod 12 has been fabricated.

In certain embodiments, mechanisms are provided to automate redressing of the grinding wheel 46 while the wheel is rotating without having to remove the wheel 46 from the machining apparatus 20. Furthermore, the dressing mechanism (not shown) performing the sharpening may be programmable to control the motion of the dressing mechanism. Thus, the dressing mechanism may be able to form desired contours on the grinding wheel 46 leading to alternate configurations of fabricated instruments. In an alternate embodiment, the dressing mechanism may be constantly sharpening the grinding wheel 46 with each rotation of the wheel while the machining apparatus continues to fabricate instruments. Furthermore, the CNC machining system can keep calculations of the amount of material taken off of the grinding wheel 46 during the redressing cycle. As such, the CNC machining system may automatically recalibrate the machining apparatus 20 and its operating parameters to take into account of the decreasing diameter of the grinding wheel 46.

Referring back to FIG. 2, the machining apparatus 20 and associated CNC machining system includes an interactive computer interface 54 for controlling the fabricating process and allowing a user to easily alter operating parameters. The CNC machining system and interactive computer interface 54 for the machining apparatus 10 can serve many functions as shown in the various screen shots in FIGS. 6-14. Generally, the computer interface 54 allows for controlling the many operating parameters described above for the machining apparatus 10. In a preferred embodiment, the settings for different instrument configurations are saved in the memory of the computer system, and a particular configuration can be selected for fabrication from the computer interface 54. The machining apparatus 20 may then fabricate the rod according to the settings in the computer systems memory. The settings for the machining apparatus 20 or cutting variables can also be changed from the computer interface.

Figure 6:
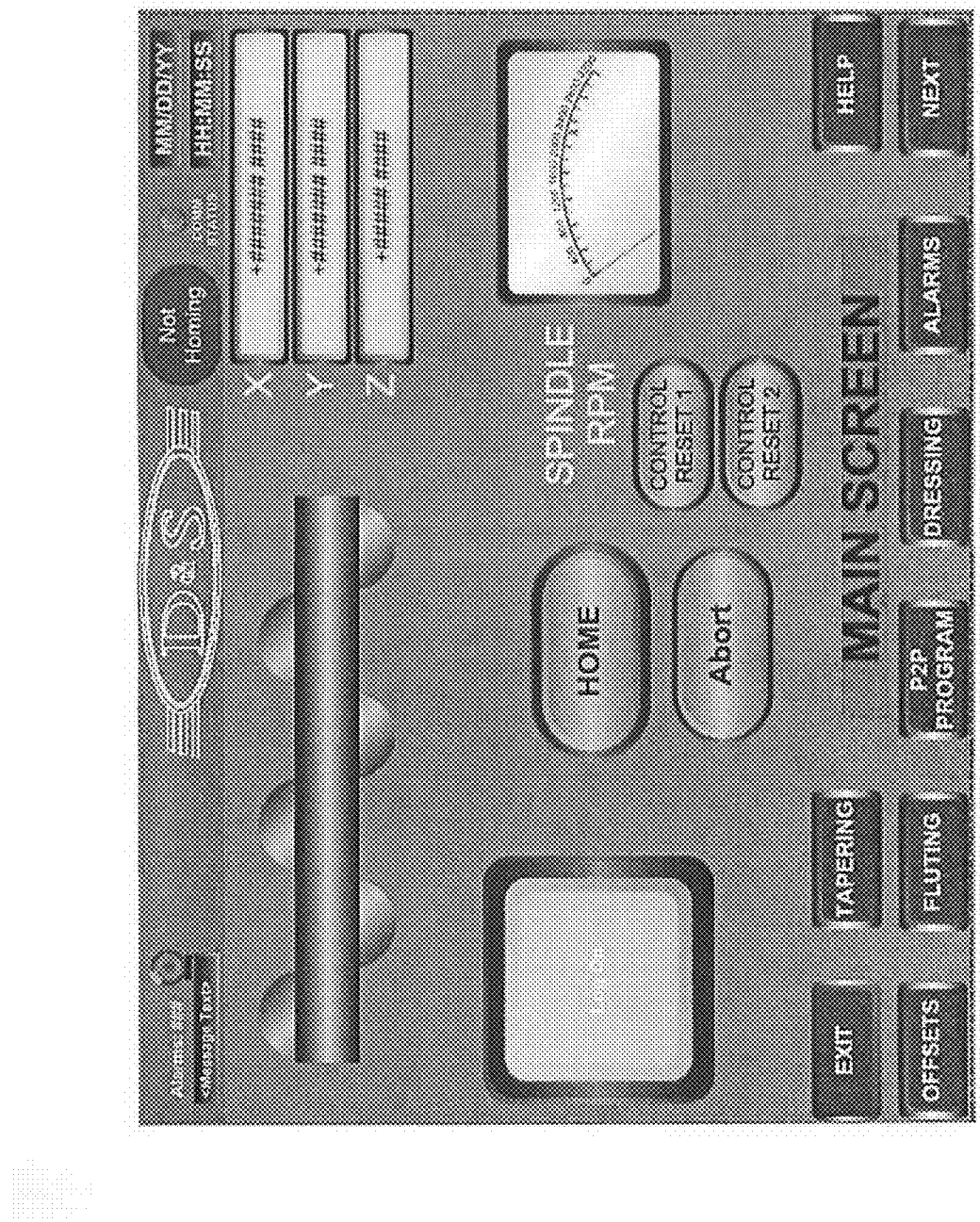
FIG. 6 depicts a main screen of an interactive computer interface according to embodiments of the present invention.
Figure 7:
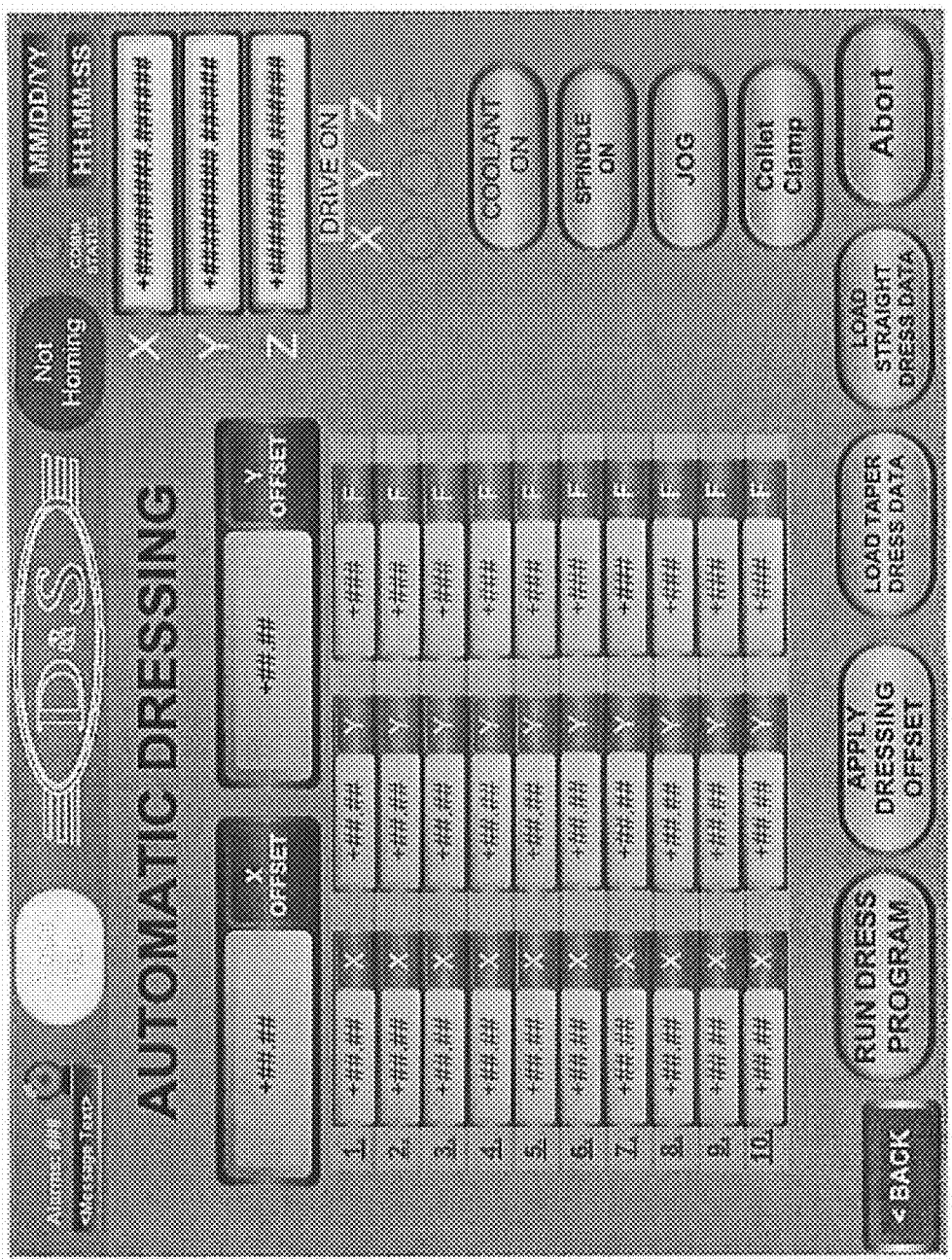
FIG. 7 depicts an automatic wheel dressing dashboard of an interactive computer interface according to embodiments of the present invention.
Figure 8:
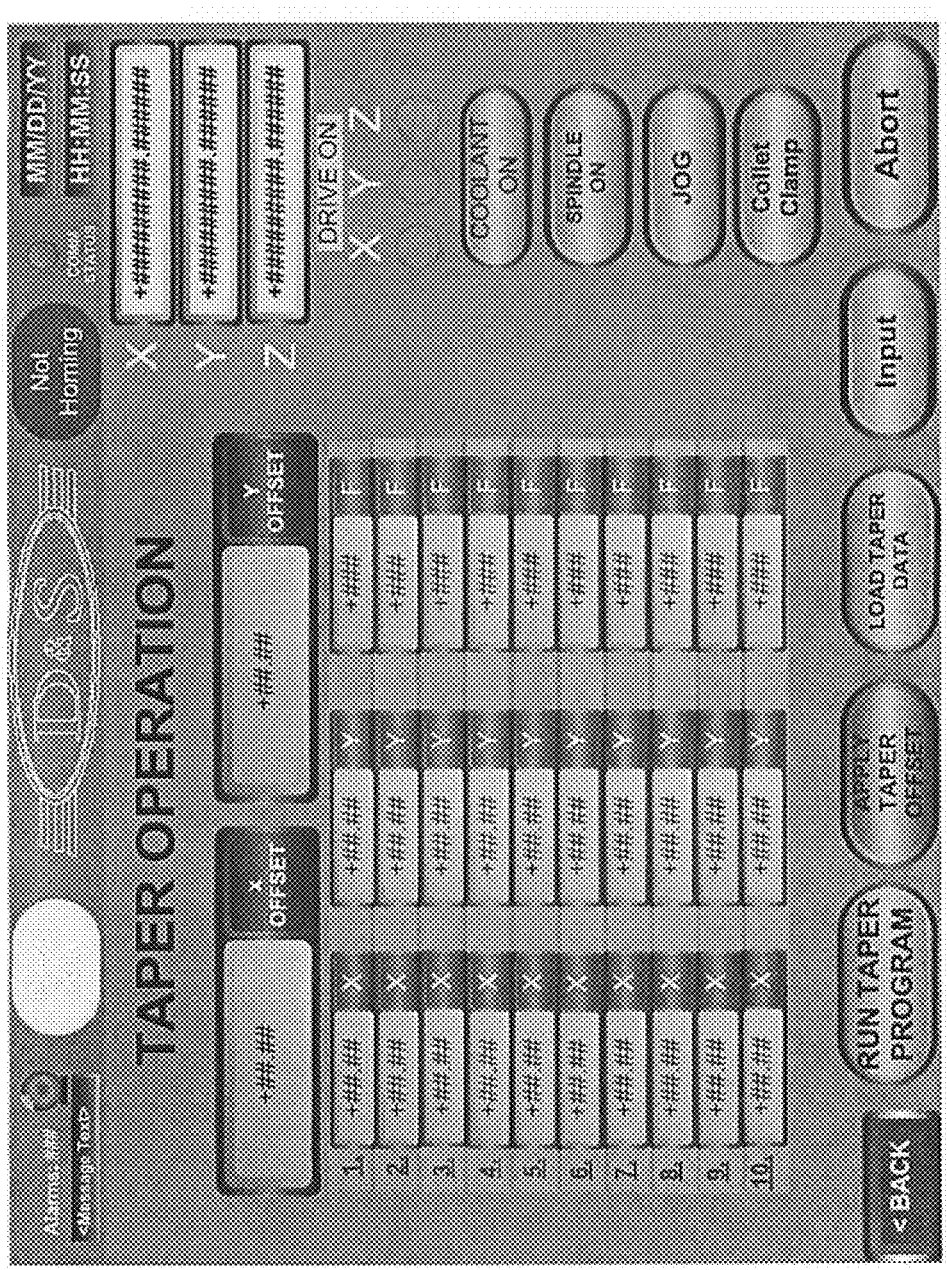
FIG. 8 depicts an automatic tapering dashboard of an interactive computer interface according to embodiments of the present invention.
Figure 9:
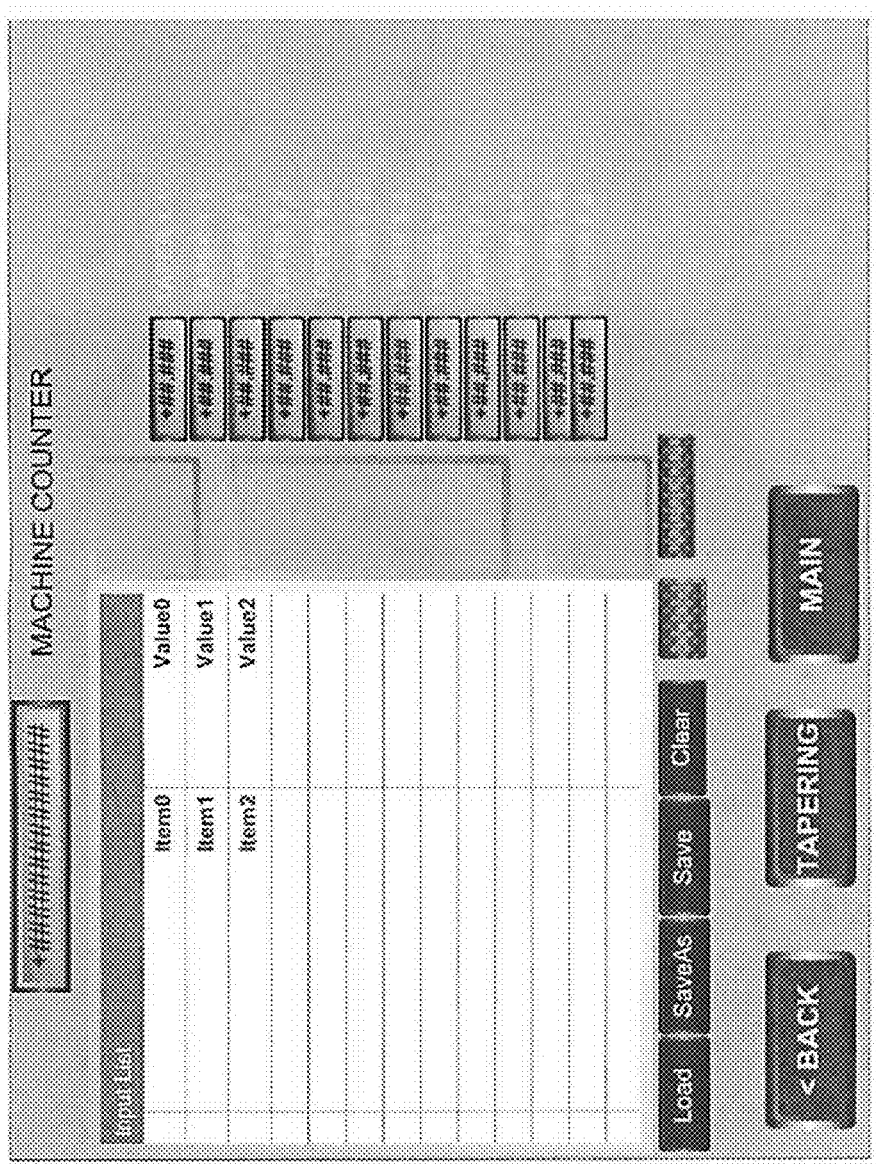
FIG. 9 depicts a tapering input dashboard of an interactive computer interface according to embodiments of the present invention.
Figure 14:
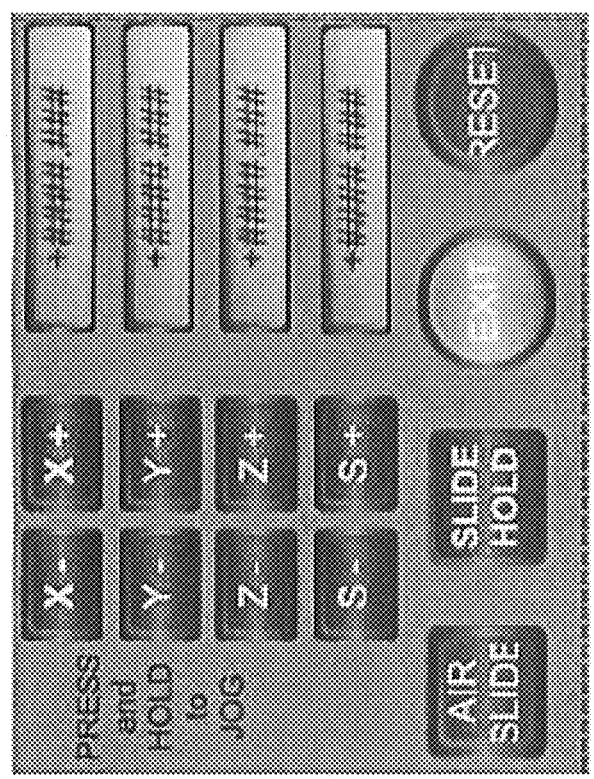
FIG. 14 depicts a jog dashboard of an interactive computer interface according to embodiments of the present invention.

The main screen or log-in screen for the interactive computer interface 54 is shown in FIG. 6. From the main screen, a user may perform various functions. For example, the user may decide to load rods 12 into the axial feed block 38, begin rotating the grinding wheel 46 by turning the spindle 48 on, and "home" the machine by sending its components to the center zero of each axis. The user may also choose which application the user would like to perform by accessing various dashboards corresponding to a chosen application. These dashboards may include an automatic wheel dressing dashboard (FIG. 7) for controlling the automated wheel dressing functions described above, an automatic tapering dashboard (FIG. 8) for tapering instruments 10 on the same machining apparatus 20, an automatic fluting dashboard (FIG. 10) for applying the chosen flute specifications to the rod 12, and a programmable automatic point to point (P2P) custom dashboard (FIG. 12) for displaying and editing the operating parameters for custom grooving, custom fluting, custom shafting, etc. An offset dashboard (FIG. 13) is also accessible for programming and applying stored offsets that are used to reposition the machine's components based on the chosen application and to adjust for variations in the dimensions of the rods 12 to be fabricated, tool wear, etc. A jog dashboard as shown in FIG. 14 is preferably accessible from each of the above dashboards for manually editing operating parameters and establishing offsets.

In accordance with the machining apparatus 20 described above with respect to FIGS. 2-5, a preferred embodiment of the method of fabricating endodontic instruments can be described. While a method of fabricating the configuration of the instrument 10 as illustrated in FIG. 1B will be described, it will be understood that many other configurations and instruments of composed of all types of metals are possible using the same machining apparatus 10. In the embodiment of FIG. 1B, the instrument 10 is tapered and includes helical flutes 16, 18. The taper of the working length 14 of the rod 12 may be done on the same machining apparatus 20 or on a centerless grinding apparatus (not shown) before machining the flutes onto the rods 12.

Figure 10:
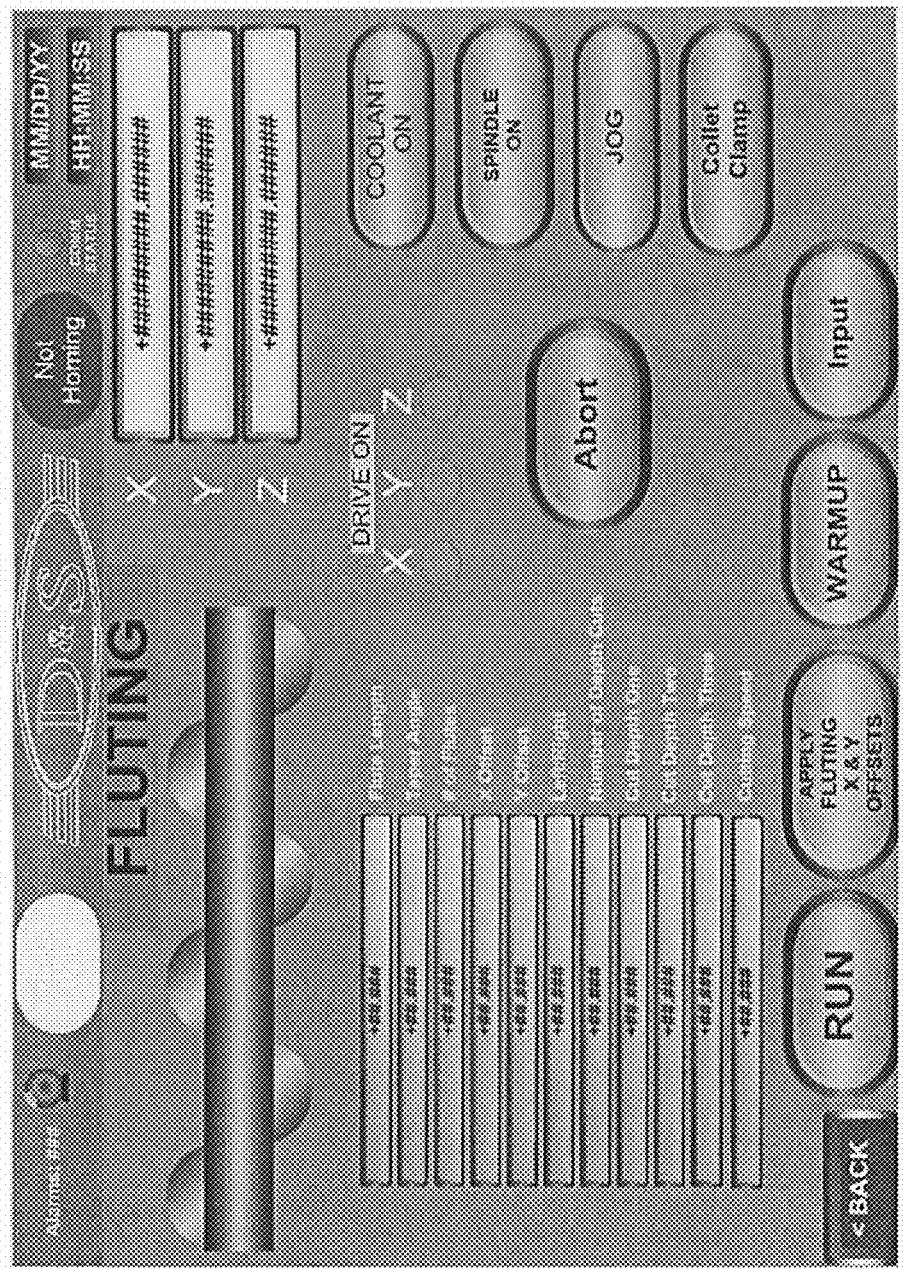
FIG. 10 depicts an automatic fluting dashboard of an interactive computer interface according to embodiments of the present invention.
Figure 11:
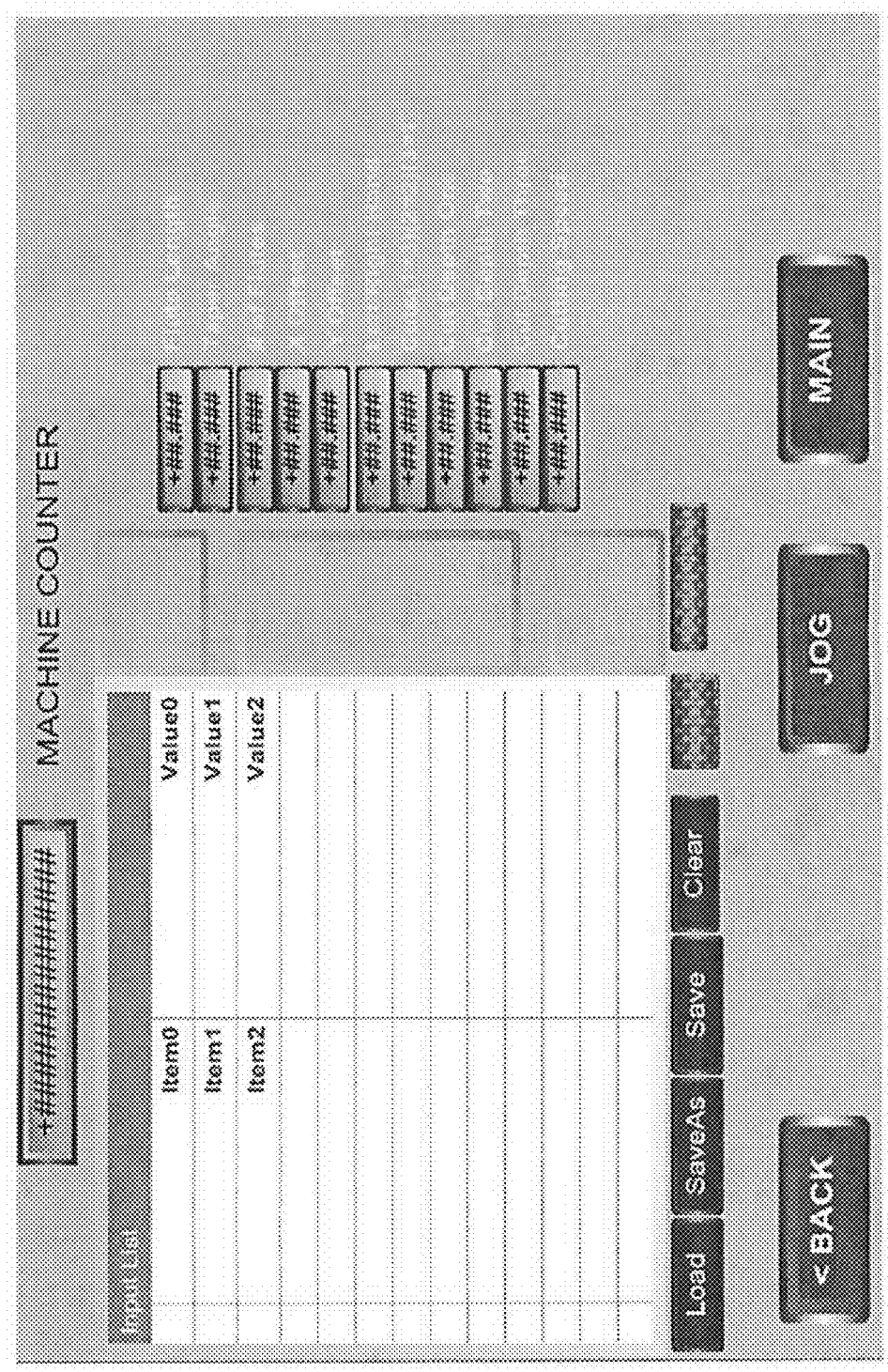
FIG. 11 depicts a fluting input dashboard of an interactive computer interface according to embodiments of the present invention.
Figure 12:
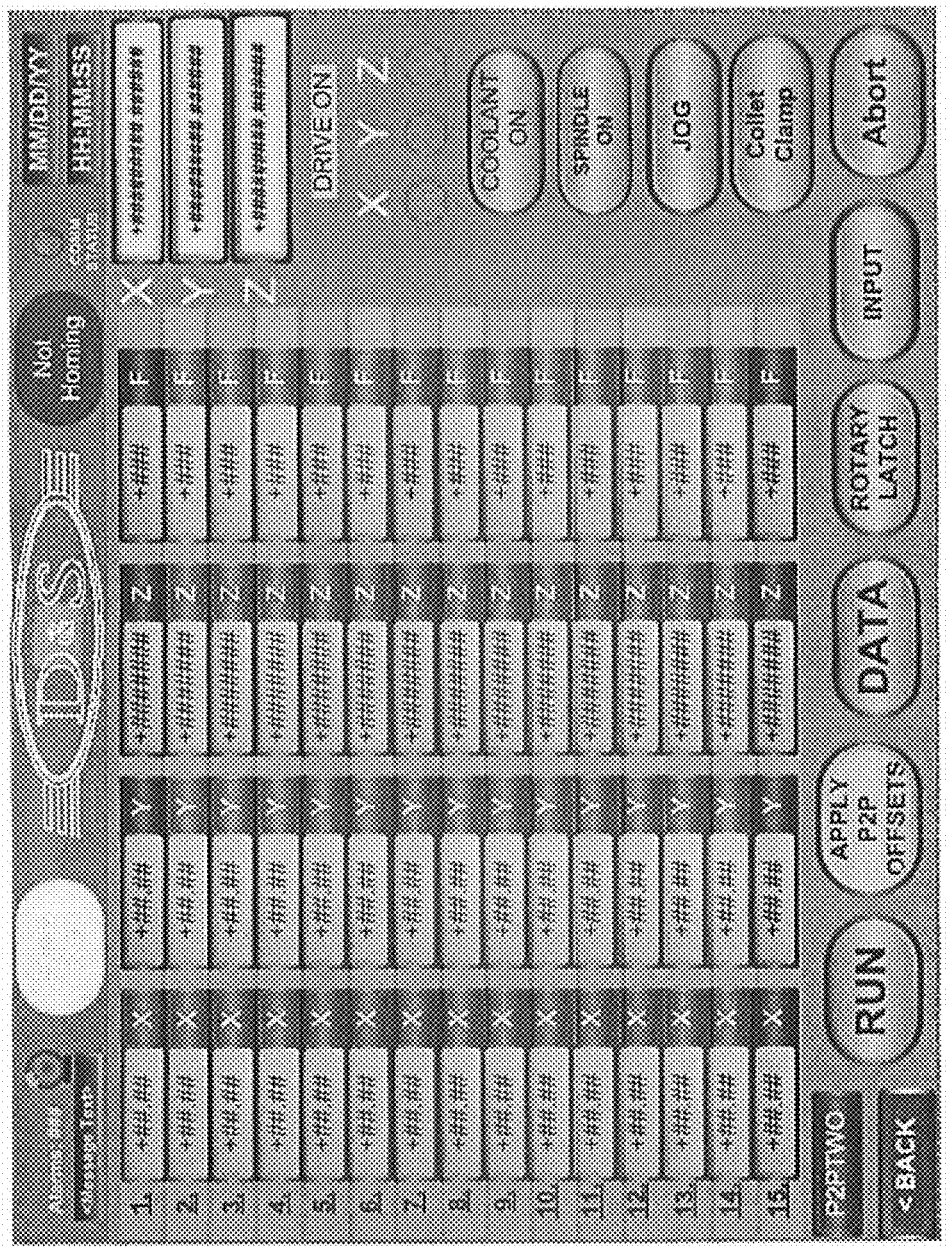
FIG. 12 depicts a programmable automatic point to point custom dashboard of an interactive computer interface according to embodiments of the present invention.
Figure 13:
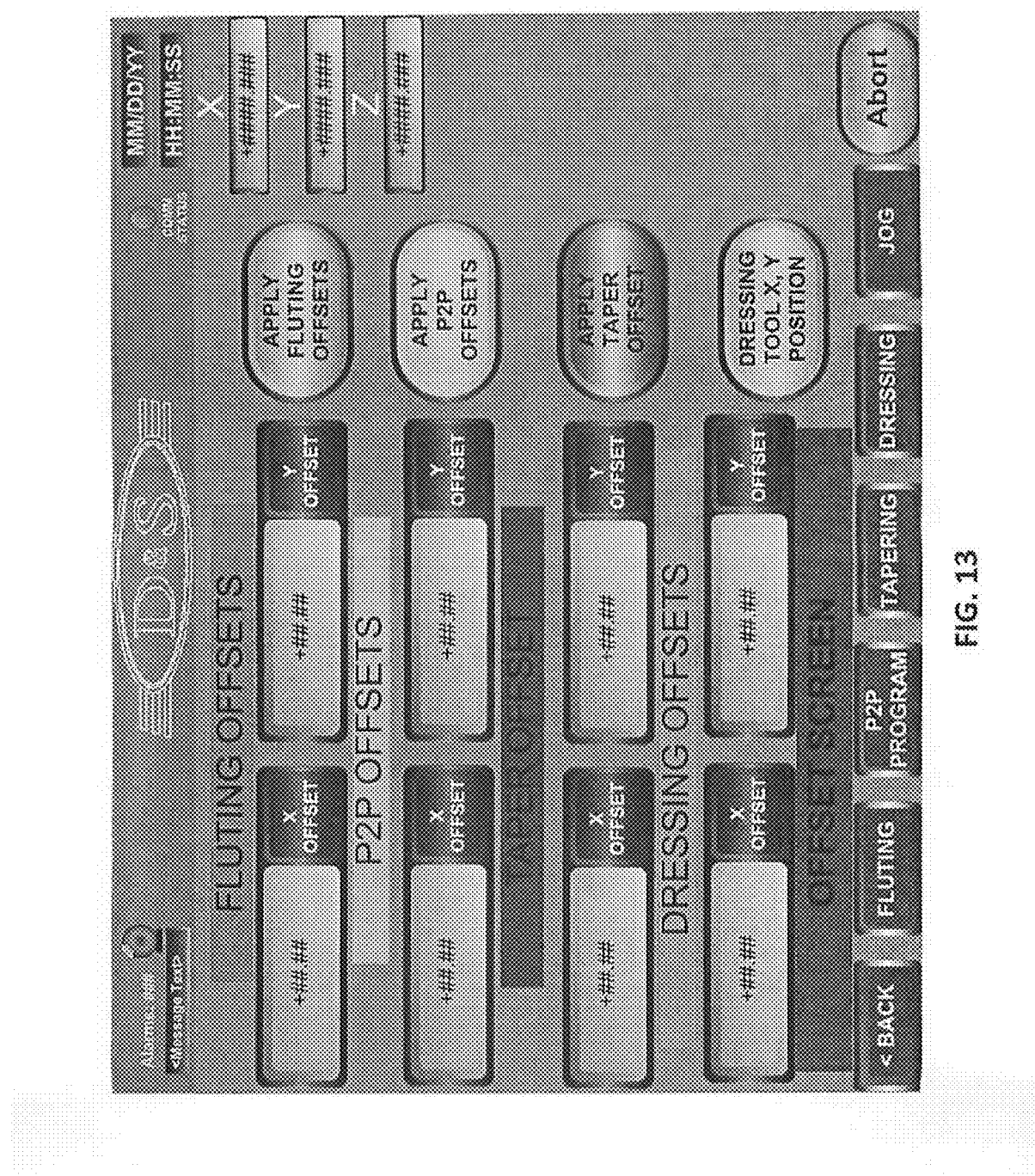
FIG. 13 depicts an offset dashboard of an interactive computer interface according to embodiments of the present invention.

To begin fabrication, the user preferably "homes" the machining apparatus 20 by sending the machine to the center zero of each axis. The user then chooses the automatic fluting dashboard as shown in FIG. 10. After loading a rod 12 into the axial feed block 38 and choosing the appropriate offset for the tapering application, the user may select the "input" button to access a fluting input dashboard as shown in FIG. 11. From the fluting input dashboard, the user can select from the input list a desired instrument configuration to be fabricated by choosing from a choice of pre-saved files (i.e. Item 0, Item 1, Item 2) containing the necessary operating parameters for fabricating the instrument 10. The user may select pre-saved files based on various instrument properties such as the diameter and taper of the rod, the length of the desired working portion, and the helix angle, pitch, and shape of the desired cutting surfaces and other instrument configuration options. The operating parameters control the movement of the rod in the X, Y, and Z axes at each point along the rod as it passes by the grinding wheel. The operating parameters may also control the rotation of the grinding wheel.

In a preferred embodiment, all the settings needed to fabricate the instrument 10 are stored in the computer system and the operator will not have to make any changes to the settings or cutting variables. However, the user may choose to alter some of the operating parameters or adjust the settings, which can be done by accessing the P2P dashboard or directly editing the stored settings using the jog dashboard, based on factors such as the diameter of the instrument to be fabricated. The loading of the rod 12 may be done by means for automatically separating and feeding the rod 12 into the axial feed block 38 or the rod 12 may be manually inserted.

The axial feed block 38 begins rotating the rod 12 about an axis preferably substantially parallel to the axis of the rotating grinding wheel 46. After the pneumatic actuator 26 is moved to the engaged position, the apparatus advances the rotating rod 12 toward the grinding wheel 46 according to the settings of the X, Y, and Z coordinates and the operating parameters stored in the pre-saved file. The linear driving mechanism 22 advances the axial feed block 38 in the X-direction according to the constant or variable feed rate as saved in the operating parameters while the lift mechanism 24 is operable to precisely control the movement of the feed block 38 in the Y coordinate direction as described above. The rotating rod 12, which is controlled by the Z coordinates, is thus moved past the grinding wheel 46 to cause a first working surface of the rod 12 to assume a helical or other desired configuration. If needed, the same working surface may be again advanced past the grinding wheel 46 to remove any cutting errors or more precisely form the working surface.

After the rod 12 has advanced past the grinding wheel 46 to form the first working surface, the feed block 38 may be lowered by the lift mechanism 24 and moved rearward by the linear driving mechanism 22. The rod 12 is then automatically indexed about its z-axis according to the settings stored in the computer system for the configuration chosen to be fabricated. Since the instrument as illustrated in FIG. 1 has two flutes, the rod's starting position about the z-axis for forming the second flute would be indexed 180° from the starting position of the rod in the z-axis for forming the first working surface. If the instrument were to have three flutes, the rod would be indexed 120° for the second surface. Thereafter, the rotating rod advances past the grinding wheel 46 to form the second surface.

Following the grinding process, the instrument 10 is removed from the machining apparatus 20. In one embodiment, the removal will be accomplished by automatic unloading utilizing a series of pneumatic slides or robotic arms that will retrieve the finished instrument 10 from the machining apparatus 20. In alternate embodiments, the instrument 10 will be manually removed. During the unloading process, the instrument 10 may be inspected for quality and accuracy by passing through a laser or camera inspection system. If the instrument 10 is satisfactory, the machining apparatus continues and loads another rod 12 into the spindle 42 for fabrication according to the same settings and operating parameters. However, if the part is not satisfactory, an alarm may be produced that is visible on the computer interface 54 and saved to other alarm dashboards to notify the operator that something is wrong with the instruments being fabricated.

The above described method is repeated to produce the desired amount of instruments for the current settings. At any time, the settings for the machining apparatus can be changed by simply selecting an instrument 10 of a different configuration from the interactive computer interface 54. Thus, one machine can be utilized for fabrication of instruments with varying configurations while operator interaction is minimized.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention.

What is claimed is:

1. A machining apparatus for fabricating endodontic instruments having a plurality of instrument configurations comprising: a computer interface for storing operating parameters of a plurality of cutting configurations, each cutting configuration corresponding to at least one of the plurality of instrument configurations, for selecting one of the plurality of cutting configurations, and for generating control signals based upon the stored operating parameters of the cutting configuration selected; a grinding wheel for grinding the endodontic instruments; and a positioning mechanism for loading one of the endodontic instruments, for receiving the control signals, and for controlling a translational motion and a rotational velocity of the loaded endodontic instrument as the loaded endodontic instrument is moved past the grinding wheel at least in part in response to the control signals; wherein the positioning mechanism further comprises: a linear driving mechanism for providing the translational motion of the positioning mechanism along a horizontal axis; a lift mechanism for providing the translational motion of the positioning mechanism along a vertical axis; and a feed block having a spindle for supporting the loaded endodontic instrument and for providing the rotational velocity of the loaded endodontic instrument.

2. The machining apparatus of claim 1 wherein the grinding wheel is disposed on a fixed spindle so that the grinding wheel is in a fixed position operable for fabricating each of the plurality of instrument configurations.

3. The machining apparatus of claim 1 wherein the linear driving mechanism includes a positioning plate disposed on a top surface of the linear driving mechanism for supporting the lift mechanism.

4. The machining apparatus of claim 1 wherein the positioning mechanism further comprises a pneumatic actuator having a mounting surface disposed on a top surface of the pneumatic actuator for mounting the feed block, the pneumatic actuator for providing positioning of the feed block in one of an engaged position adjacent the grinding wheel and a disengaged position remote from the grinding wheel.

5. The machining apparatus of claim 1 further comprising a dressing mechanism disposed adjacent the grinding wheel for redressing the grinding wheel, the computer interface for storing measurement calculations of a diameter of the grinding wheel during redressing and for recalibrating the operating parameters of the plurality of cutting configurations based on the measurement calculations.

6. The machining apparatus of claim 1 wherein the computer interface includes a jog dashboard for manually editing the stored operating parameters of the plurality of cutting configurations.

7. The machining apparatus of claim 1 wherein the positioning mechanism includes a loading mechanism for automatically loading the endodontic instrument into the positioning mechanism.

8. The machining apparatus of claim 1 wherein the computer interface is operable for storing operating parameters of a plurality of tapering configurations, for selecting one of the plurality of tapering configurations, and for generating control signals based upon the stored operating parameters of the tapering configuration selected for moving the loaded endodontic instrument past the grinding wheel for tapering the loaded endodontic instrument prior to moving the loaded endodontic instrument past the grinding wheel for fluting the loaded endodontic instrument.

9. A machining apparatus for fabricating endodontic instruments having a plurality of instrument configurations comprising:
a computer interface for storing operating parameters of a plurality of cutting configurations, each cutting configuration corresponding to at least one of the plurality of instrument configurations, for selecting one of the plurality of cutting configurations, and for generating control signals based upon the stored operating parameters of the cutting configuration selected;
a grinding wheel disposed on a fixed spindle so that the grinding wheel is in a fixed position operable for fabricating each of the plurality of instrument configurations; and a positioning mechanism for receiving the control signals and for controlling a translational motion and a rotational velocity of the positioning mechanism, the positioning mechanism including: a linear driving mechanism for providing the translational motion of the positioning mechanism along a horizontal axis based at least in part on the control signals, a lift mechanism for providing the translational motion of the positioning mechanism along a vertical axis at least in part on the control signals, and a feed block having a spindle for loading an endodontic instrument to be fabricated and for providing a rotational velocity of the loaded endodontic instrument based at least in part on the control signals, the feed block for moving the loaded endodontic instrument past the grinding wheel based at least in part on the cutting configuration selected; wherein the stored operating parameters of the plurality of cutting configurations include tapering parameters, the positioning mechanism for moving the loaded endodontic instrument past the grinding wheel for tapering the loaded endodontic instrument according to the tapering parameters prior to moving the loaded endodontic instrument past the grinding wheel for fluting the loaded endodontic instrument.

* * * * *